(12) United States Patent
Gumpesberger

(10) Patent No.: US 7,800,740 B2
(45) Date of Patent: Sep. 21, 2010

(54) METHOD AND APPARATUS FOR IDENTIFYING AND CHARACTERIZING OBJECTS BASED ON FLUORESCENCE

(75) Inventor: Sylvia Gumpesberger, 9 Percy Street, Toronto (CA) M5A 3M7

(73) Assignee: Sylvia Gumpesberger, Toronto (CA)

( * ) Notice: Subject to any disclaimer, the term of this patent is extended or adjusted under 35 U.S.C. 154(b) by 472 days.

(21) Appl. No.: 11/844,755

(22) Filed: Aug. 24, 2007

(65) Prior Publication Data
US 2009/0051897 A1 Feb. 26, 2009

(51) Int. Cl.
*G01N 21/00* (2006.01)
(52) U.S. Cl. .......................... 356/30; 356/317
(58) Field of Classification Search ............ 356/30, 356/317
See application file for complete search history.

(56) References Cited

U.S. PATENT DOCUMENTS 5,351,117 A * 9/1994 Stewart et al. ............... 356/30
5,801,819 A * 9/1998 Spear et al. ................... 356/30
6,014,208 A * 1/2000 Welbourn et al. ......... 356/237.1
2002/0089658 A1* 7/2002 Seville ........................ 355/113
2005/0006596 A1* 1/2005 Kanai ....................... 250/458.1
2007/0109536 A1* 5/2007 Weiss et al. ................. 356/318

\* cited by examiner

*Primary Examiner*—Kara E Geisel
(74) *Attorney, Agent, or Firm*—Vidas, Arrett & Steinkraus

(57) ABSTRACT

A method and apparatus for characterizing objects. The method includes the steps of illuminating the object with incident red light having at least some wavelengths between 620 nms and 650 nms and detecting red light fluorescence from said object having a wavelength greater than visible wavelengths greater than that of the incident wavelengths, for example by using a filter. An apparatus including a source of red incident light, a detector for longer wavelength fluorescent light and a means for physically removing the detected objects from the rest is also provided. An embodiment of the present invention may be used in a mine, for example, to separate gem stones from less valuable ore rock or in prospecting to detect the presence of gems. In this embodiment the detection is not possible with the naked eye alone.

17 Claims, 8 Drawing Sheets

METHOD AND APPARATUS FOR IDENTIFYING AND CHARACTERIZING OBJECTS BASED ON FLUORESCENCE

FIELD OF THE INVENTION

This invention relates the general field of identification or sorting technologies, and particularly relates to identification or sorting technologies which involve exposing the material to be identified or sorted to an incident beam of electromagnetic radiation. Most particularly this invention relates to identification or sorting based on detecting a material's fluorescent reaction to the incident energy beam.

BACKGROUND OF THE INVENTION

Electromagnetic radiation, and in particular various wavelengths of light, may be used to identify or sort various materials. One problem in material sorting relates to identifying gems. It can be difficult to identify different gems from the ore in which they are originally found or from various types of look alike material, such as glass or man made materials that may be used to imitate a gem, for example. Not all look-alike materials can be identified by any one test, and it is common in gemology to put a suspect material through a series of identification tests to properly identify and certify that the gem in question is genuine.

Many different techniques and devices exist for the identification of gems by fluorescence. The most prominent testing techniques involve using UV light or X-rays, although other excitation methods are also known. For example, U.S. Pat. No. 883,653 teaches using a blue incident light of a higher refrangibility to produce fluorescence of a lower refrangibility and to obviate the masking effect of the reflected light by using a second ray filter of the yellow colour to transmit red, orange yellow, yellow green and green fluorescence. However, in blue light, red orange yellow, green and green fluorescence are not necessarily masked by the blue light, and due to the large wavelength difference between the incident and fluorescing wavelengths, a simple or crude filter will work well to separate the incident light from the fluorescence.

U.S. Pat. No. 4,394,580 uses absorption, internal reflection and internal excitation to try to characterize gems. However, this invention teaches a wide source i.e. white light, and the use of red and green optical filters before a detector. However, the red and green gems could also be visible in the white spectrum light to the naked eye. Further, of course white light covers the visible light spectrum including red fluorescent wavelengths so any fluorescing will be masked by white light, even if a filter is used.

U.S. Pat. No. 5,118,181 relates to a method of identifying individual gemstones by using a series of specific incident light wavelengths in the ultraviolet or infra red spectrum and measuring the response of the gem stone to each separate wavelength. While useful to characterize a particular stone, this cannot be used in a mine environment to separate gem stones from ore for example.

Another previously known technique for identifying gems has been to detect the presence of fluorescing material such as found in certain gems containing the element Chromium. Such gems can red fluoresce when exposed to particular light frequencies, and examples of gems which can fluoresce red include emeralds, rubies and the like. In the past the fluorescence was detected by using ultraviolet light, or even an incident blue light on the gem in question. What has been previously known is that such incident light can elicit the red light fluorescence from specific gems, which could then be characterized based on the presence of such red light fluorescence. The blue incident light can be obtained by shining a white light through a blue liquid onto the object in question, although more recently it is more common to use a blue light source such as an LED. Longwave UV LEDs exist also. The technique uses incident light having wavelengths much shorter than the red light fluorescence, making the red light fluorescence easier to detect. It has also been understood up until now that while UV and blue light elicit a relatively strong and easily detectable red light fluorescence, wavelengths closer to the fluorescing wavelengths tend to exhibit a weaker and more muted excitation response. The use of a blue filter would of course eliminate red light wavelengths from the incident light. When the object is viewed through a red light filter, which blocks out the blue or UV incident light, the red fluorescence is then visible. In many cases strong fluorescence can be detected which is easily identified by eye, or even through the use of a crude filter which broadly transmits red light.

While blue or ultraviolet incident light works well in some circumstances, the use of these incident lights to elicit a red light luminescence is problematic in certain situations. For example, in underground mining of precious gem materials, it is not desirable for the mine workers to be able to easily identify the individual gemstones. These tend to be both small and very valuable so the use of any detecting method that makes the gems more apparent to the visible eye, or easily identifiable through the use of a crude filter is not desirable as valuable gemstones can go missing. So, blue, ultraviolet or even wide spectrum white lights all of which can make gem material visible to the naked eye, are not the most desirable form of incident light for sorting the gems from the background ore in a mine environment.

What is desired is a simple and easy way to use the red fluorescence of certain materials to characterize the material, without necessarily revealing the property of even the body colour of the material to the naked eye or making it easily detectable with a crude filter.

SUMMARY OF THE INVENTION

The present invention is directed to a method of sorting out material based on its red light fluorescent properties. However, rather than using blue, ultraviolet or white incident light, the present invention is directed to using red incident light to excite the material being identified to cause it to fluoresce. In particular, the red light source will cause fluorescence to arise in a wavelength band only slightly above the red light wavelength band of the preferred incident light source, and thus can be used to characterize and identify the presence of a certain fluorescing material, based solely on the fluorescing property. However, the use of a red incident light means that the unfiltered red fluorescence will be completely swamped by the red reflected light and the red fluorescence of the gemstones will remain invisible to the naked eye. Further, the red fluorescing light is separated from the red incident light by a relatively small difference in wavelength, and is much harder to detect, requiring a much more specific filter. Thus, separating gemstones from the ore, without the use of the specific filter capable of blocking incident red light, but passing fluorescence having only slightly longer wavelengths is much more difficult. In this way the valuable gem materials are only visible to the appropriate people through the use of an appropriate filter or detection means.

For example, in a mine environment, the use of a narrow band red light source, such as an LED will not permit a red fluorescence light response to be visible the naked eye but will be easily detectable by the presence of the higher wavelength fluorescence by means of a wavelength detector or even by visual examination with an appropriate narrow band filter.

Thus, the present invention provides a method which is particularly useful in being able to sort material, for example, when trying to select the gem materials from a background such as common ore. Although the use of red light causes the gem to fluorescence in the longer wavelength red light spectrum, this fluorescing is masked by the incident light to the naked eye. However, by means of a detector or through the use of a specific red light filter, the fluorescence can be detected and this can be used as the basis for sorting the gem material from the ore.

Therefore there is provided, according to one aspect of the present invention, a method of characterizing objects, said method comprising the steps of:

illuminating said object with an incident red light having wavelengths shorter than a maximum red light wavelength, said object being characterized as exhibiting red light fluorescence of a longer wavelength than the wavelength of the incident light; and detecting the presence of said longer wavelength red light fluorescence emanating from said object.

According to a further aspect of the present invention, there is provided an apparatus for sorting materials comprising:

a source of red incident light including wavelengths of at least between 600 and 650 nms, a station to apply the red incident light to an object;

a detector to detect red light fluorescence in a wavelength between 650 as 700 nms; and a means to physically separate said object exhibiting said red light fluorescence from other objects being tested.

BRIEF DESCRIPTION OF THE DRAWINGS

Reference will now be made, by way of example only, to drawings which depict various embodiments of the present invention and in which.

DETAILED DESCRIPTION OF THE PREFERRED EMBODIMENTS

The present invention is directed to a method of identifying or detecting the presence of certain materials, based on the fluorescence of such materials under the exposure of such materials to incident red light. The term red light includes light generally in the visible light spectrum in the wavelength range of about 620 to 750 nms. Most preferably, to be easily visible, the incident light wavelength is less than about 700 nms. In this specification the term fluorescing means that electromagnetic energy is released from an object which is subject to an incident light, at a frequency that is different from the incident light. Thus fluorescing is an optical phenomenon in cold bodies in which the molecular absorption of a photon triggers the emission of another photon with a longer wavelength. This invention relates to the useful application of this phenomenon to characterize or separate articles based on specific forms of such fluorescence as described below.

Figure 1:
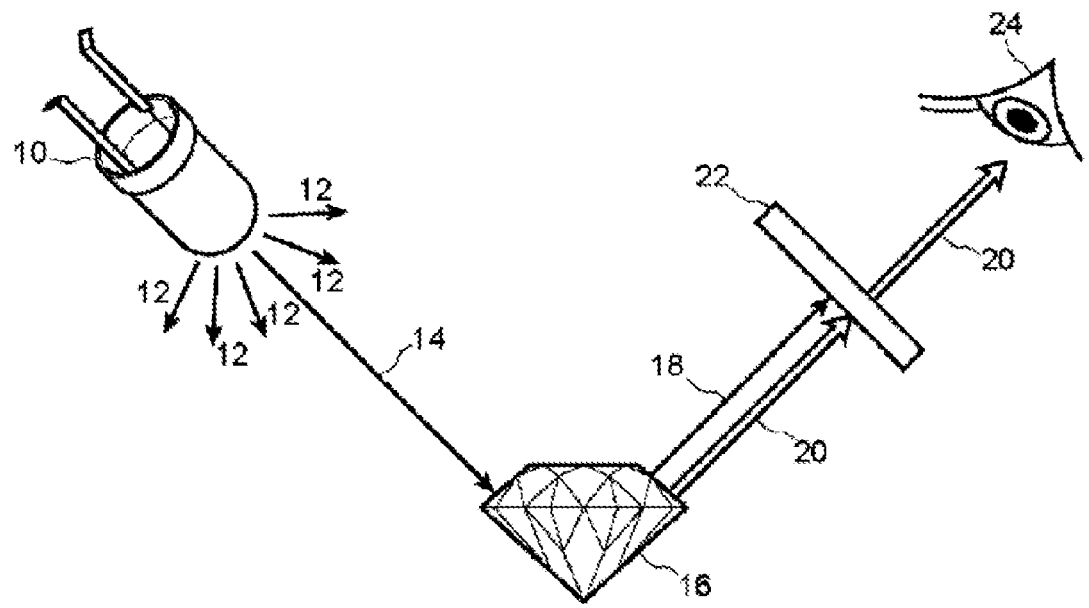
FIG. 1 is a view of the present invention according to a first embodiment.

FIG. 1 shows an example of the method of the present invention being implemented. A red light source, for example an LED, is shown at 10 with red wavelength light emanating as indicated by arrows 12. In this specification the term red is used to describe the wavelengths of the incident light, and it will be generally understood to include the wavelengths within the visible red spectrum (620-750 nms). In a preferred form of the invention a red LED is used which produces a relatively narrow range of wavelengths of light, in the 610 to 650 nanometre range, primarily within the 620 to 640 range. It will be understood by those skilled in the art that the present invention is not limited to LED's which produce photons within this specific band, provided the wavelengths of the incident light are generally within the visible red light band as explained in more detail below. For example, a red light laser having wavelengths of a narrow band peaking at 655 will also produce adequate results as explained below. Whether the light source is an LED or laser light, the light intensity will need to be sufficient to excite fluorescence which may vary from gem to gem, as will be understood by those skilled in the art. A laser light, with it is tightly focussed beam will provide good intensity at greater distances.

Turning back to FIG. 1, arrow 14 represents an incident light ray directed onto a gem 16 and produces two resultant light rays 18 and 20. The light ray 18 is simply a reflected or transmitted red light ray having the same wavelength as the incident light ray. The light ray 20 however is a fluorescent light ray which is of a different, and longer, wavelength from the reflected or transmitted light ray 18. A filter 22 is shown which blocks or absorbs the reflected or transmitted red light ray 18 but permits the fluorescent red light ray 20 to pass. The passed fluorescing light ray 20 can then be readily observed, as indicated by eye 24. Although longer than the incident light, the fluorescing light wavelength is still in the visible light spectrum.

Figure 2:
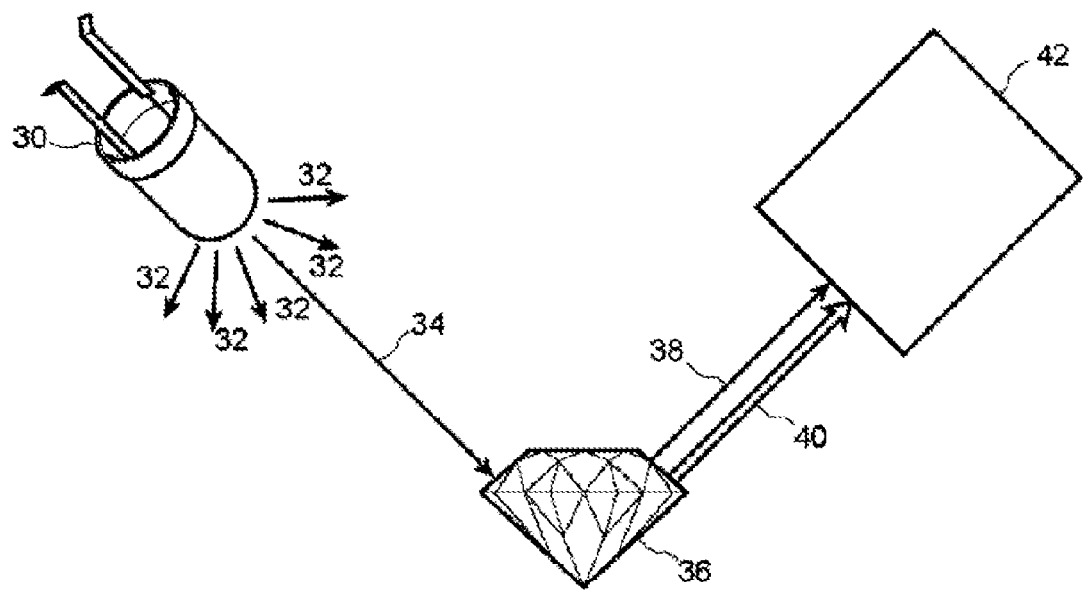
FIG. 2 is a view of the present invention according to a second embodiment.

FIG. 2 discloses a further embodiment of the present invention. In FIG. 2, the red wavelength light source is noted as 30 having a plurality of red light rays 32 emanating there-from. Again, the light rays 32 include incident red light ray 34 which impinges upon a gem 36. Two different light rays extend from the gem 36, shown as 38 and 40. The light ray 38 is merely a reflected or transmitted red light ray, whereas the light ray 40 is a fluorescent light ray having a longer wavelength than the reflected or transmitted red light ray. Both of these light rays impinge upon a detector identified by 42. The detector includes a means for detecting the presence of the longer red fluorescent wavelengths of the light ray 40, which can be used as a basis to identify the presence of red light fluorescing materials in the object or gem itself. For example, the detector can measure the wavelengths of the light emanating from the object, determine if there is a sufficient amount of longer wavelength red fluorescent light present and provide an electronic output to signify that there is. The electronic output can then be used as a trigger signal, for example for an actuator, such as an arm or a blast of compressed air, to separate the detected object from a stream of objects moving for example past the detector on a conveyor belt or other form of mover. In this way the detector can signal and separate gem bearing ore from non-gem bearing ore for example. An advantage of using a detector as described is that it can also detect red light fluorescence that may be above the easily visible red light spectrum.

A preferred light source according to the present invention is a light emitting diode or LED. An LED is a semiconductor device which often looks like a tiny light bulb without any filament. LEDs have the advantage that they do not heat up, are relatively energy efficient and have a potential life span of 100,000 hours or about 20 times longer than conventional light bulbs. While some LEDs can produce very bright white light or light of specific colours, in the present invention, it is preferred to use a somewhat monochromatic red light laser LED. A red light LED also uses less energy than an LED which produces a shorter wavelength light, such as a UV or blue light LED, leading to longer battery life for hand held red LED devices. Laser light sources are also comprehended, as providing both an intense and narrow red incident light source.

Figure 3:
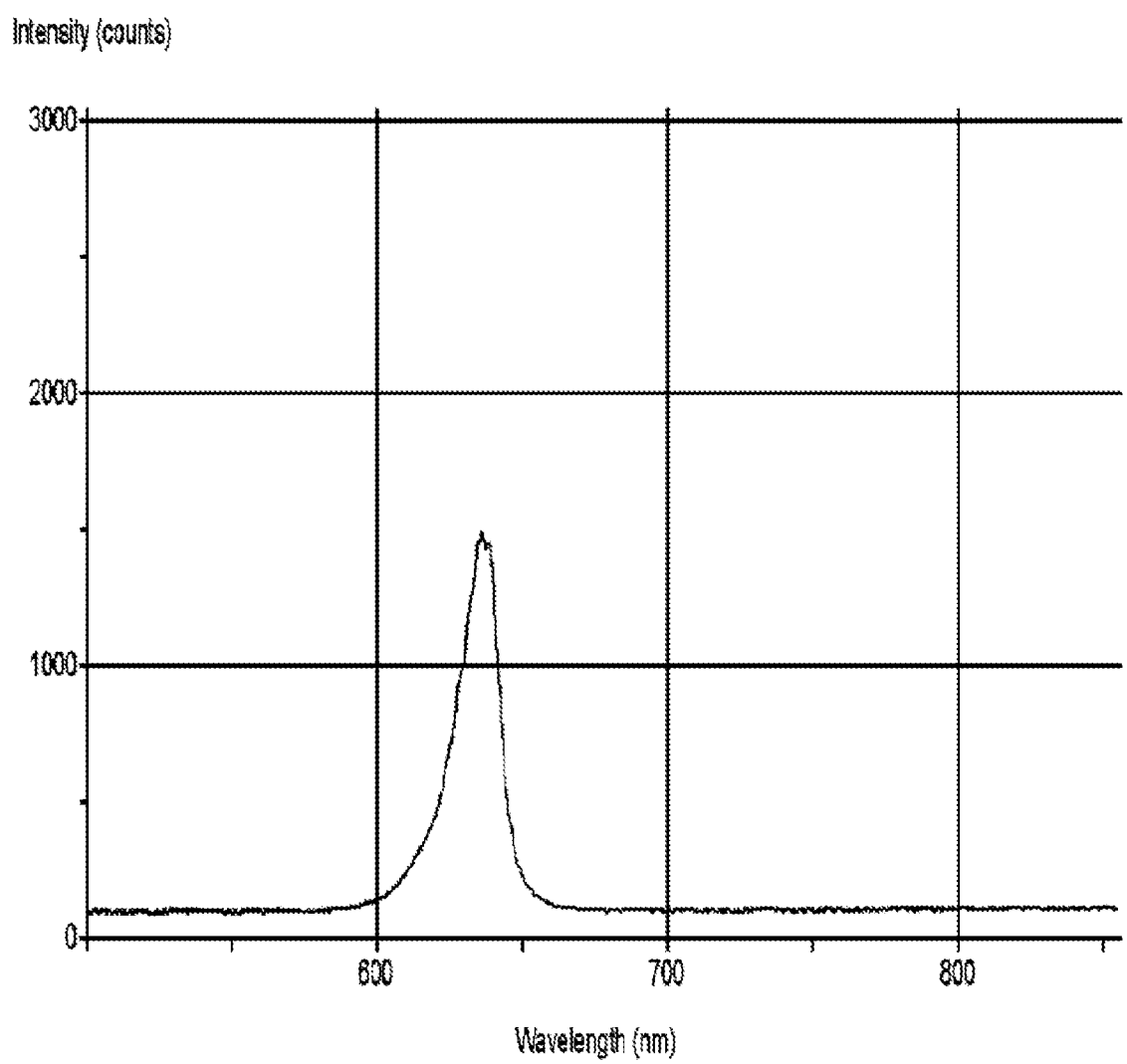
FIG. 3 is a spectrometer graph of the wavelengths and intensities of the wavelengths produced by a red LED suitable for use in the present invention.

Turning to FIG. 3, a wavelength and intensity graph for a preferred form of red LED according to the present invention is shown. As can be seen, the red light intensity peaks at approximately 635 nanometres, rising from a base line of approximately 600 nanometres and ending at a comparable base line of approximately 650 nanometres. The preferred wavelength range of this incident light source is therefore between 600 and 650 nanometres, although an even narrower or different range can also be used as will be understood from the detailed description below.

Figure 4:
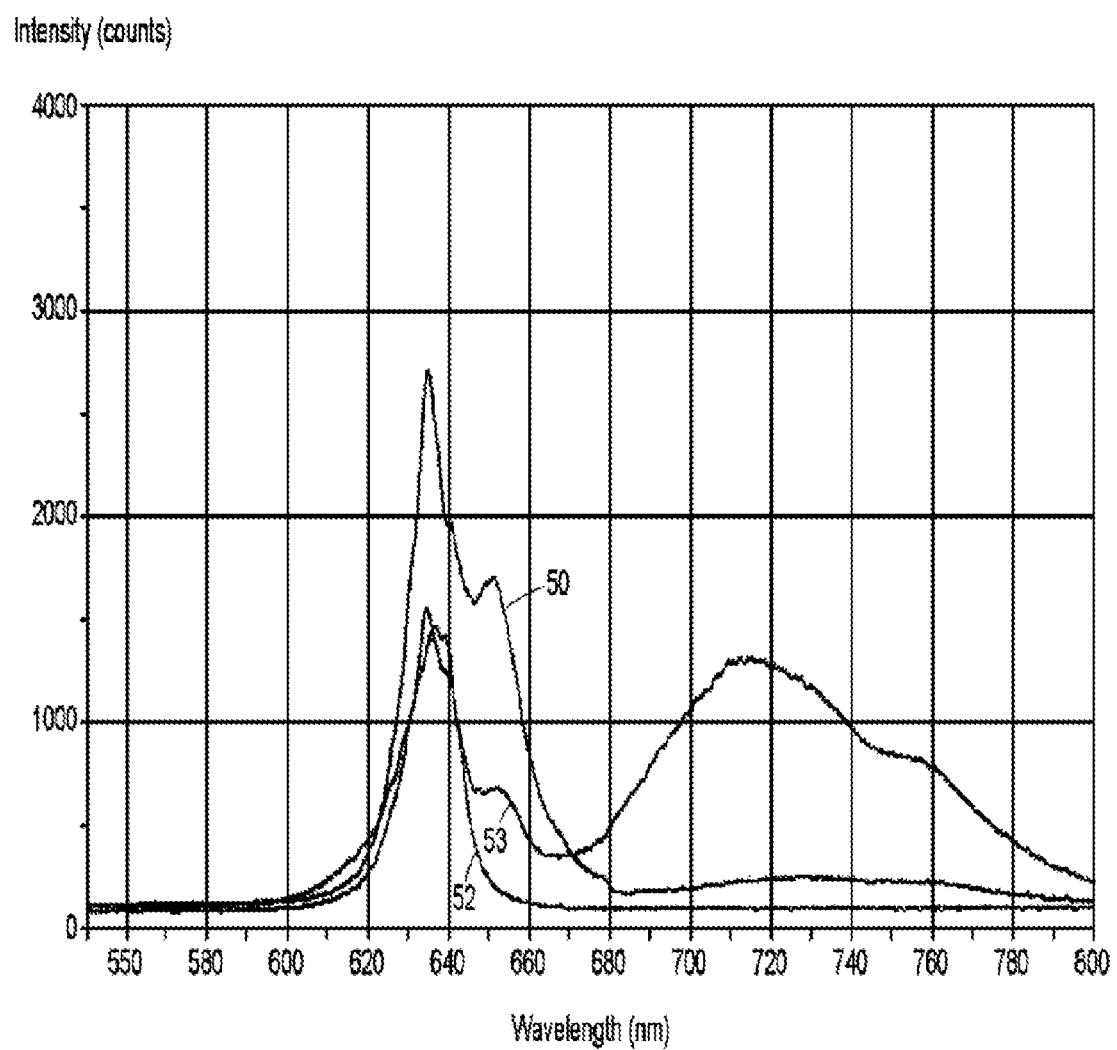
FIG. 4 is a view of the wavelength intensity graphs or the light emanating from various natural and synthetic emeralds.

FIG. 4 is a view of the wavelength and light intensity of the red light fluorescence produced by two types of emeralds when exposed to the red light LED of FIG. 3. The line 50 depicts a natural Columbian emerald and illustrates a red fluorescence light intensity sub-peak just >640 nms. This sub-peak is a fluorescence phenomenon at a longer wavelength than the incident red light, and is clearly visible when the incident red light wavelengths are filtered out. As can be seen from the graph, line 52 represents the incident red light wavelength produced by the preferred LED light source according to the present invention (and matches the plot of FIG. 3). Line 53 represents the red fluorescing light emanating from a synthetic flux emerald and includes a smaller but still visible intensity peak just beyond 650 nanometers in wavelength. In this sense synthetic means a lab grown counterpart to the natural material which is chemically, optically, chrystallographically and otherwise substantially identical to the natural gemstone. Interestingly, the synthetic emerald also includes a second intensity peak at around a wavelength of about 710 nanometers some of which is also possibly visible when the wavelengths of the incident red light are filtered out. Thus an aspect of the present invention is identifying a specific fluorescing pattern associated with a specific gem material, and separating one gem material from another based on such red light fluorescing patterns. Above 710 can be actually somewhat hard to see, but does form part of the visible red light spectrum, and can be detected by a detection device as previously described. Interestingly, in respect of natural emeralds, the intensity of the red light fluorescence produced by an incident red light source is often observed to be significantly greater than the intensity of red light fluorescence produced by a UV incident light.

Figure 5:
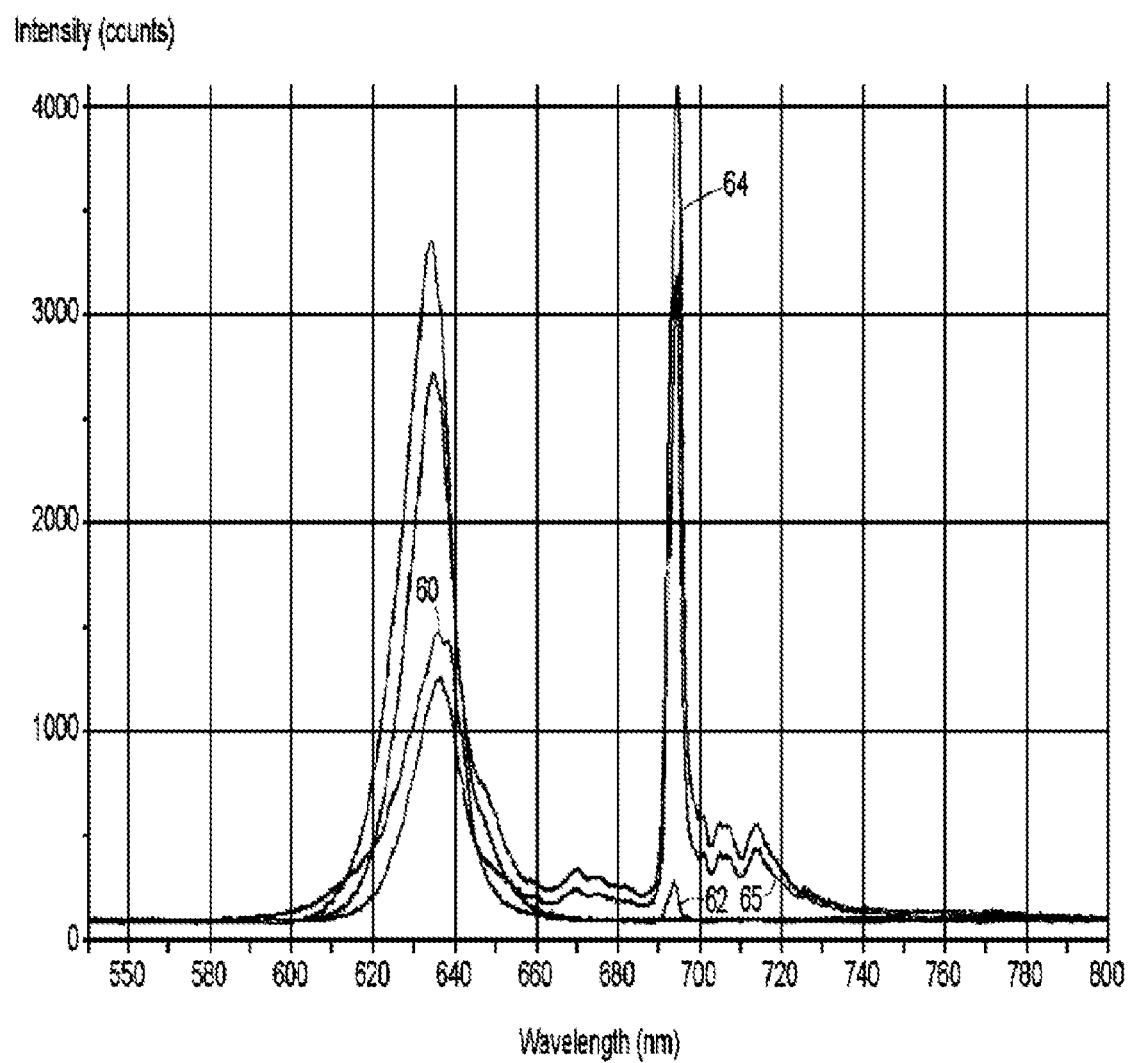
FIG. 5 is a view of the wavelength and intensity readings for the light emanating from natural and synthetic ruby based on an incident light from a red LED.

FIG. 5 is a plot or graph of the wavelength versus intensity for a number of natural and synthetic ruby elements exposed to a red light incident light source. Again, the red LED incident light source peaking at 635 nanometers is shown at line 60. A natural Be treated ruby is shown at line 62, a natural treated ruby from Burma is shown at line 64 and a synthetic flame fusion ruby is shown at line 65. Be treated rubies usually start out as a poor coloured sapphire, often iron quenched, thus explaining the poor red fluorescence shown here. The purpose of the Be treatment is to improve the colour, but it does not improve the fluorescence. As will be understood by those skilled in the art, both rubies and sapphires are classed as corundum. Rubies are red corundum and all other colours of corundum are sapphires. As can be noted, the natural ruby from Burma exhibits a high degree of fluorescence, the synthetic flame treated ruby also exhibits fluorescence, and the natural Be treated ruby exhibits a very minor fluorescence all centered around 690 nanometers. As can be seen from FIG. 5 each of these gem materials has responded by fluorescing at a red light wavelength longer than the incident light wavelengths.

Figure 6:
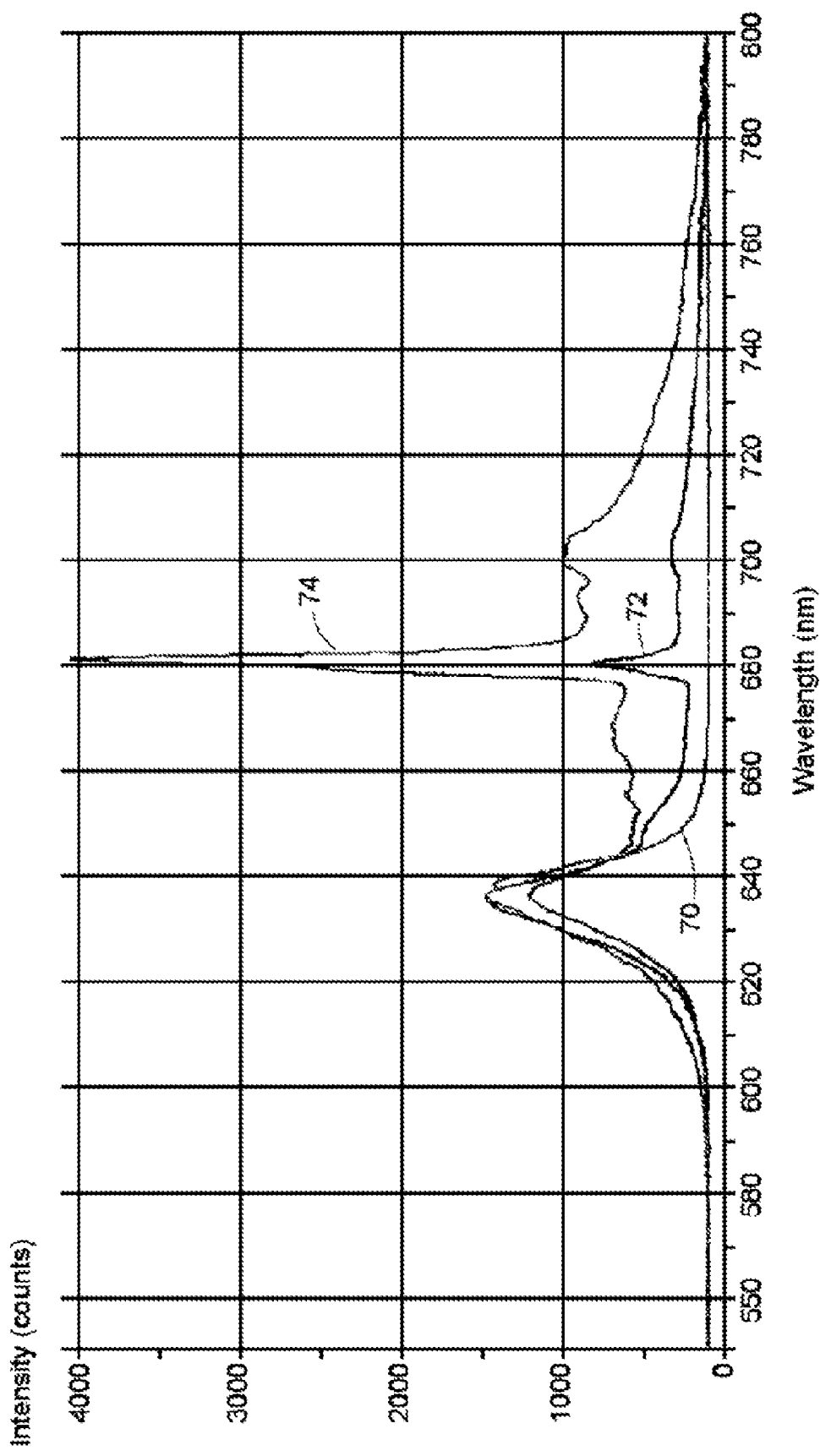
FIG. 6 is a view of the wavelengths and intensities produced by natural and synthetic alexandrite when illuminated by an incident light from a red LED.

FIG. 6 shows the wavelength and intensity graphs for natural and synthetic alexandrite exposed to incident red light. As can be seen, the red LED source peaking at 635 nanometers is shown at line 70, the natural alexandrite from India is shown at line 72 and the synthetic hydrothermal alexandrite is shown at line 74. Each of these alexandrite gems has a fluorescing peak at about 680 nanometers. The synthetic hydrothermal alexandrite has a very intense fluorescence up to 4,000 counts, whereas the natural alexandrite has a much weaker fluorescence of just under 1,000 counts. However, in each case, the longer wavelength fluorescence is clearly visible with an appropriate filter or detector capable of detecting light at the red light fluorescing wavelength peak around 680 nanometers.

Figure 7:
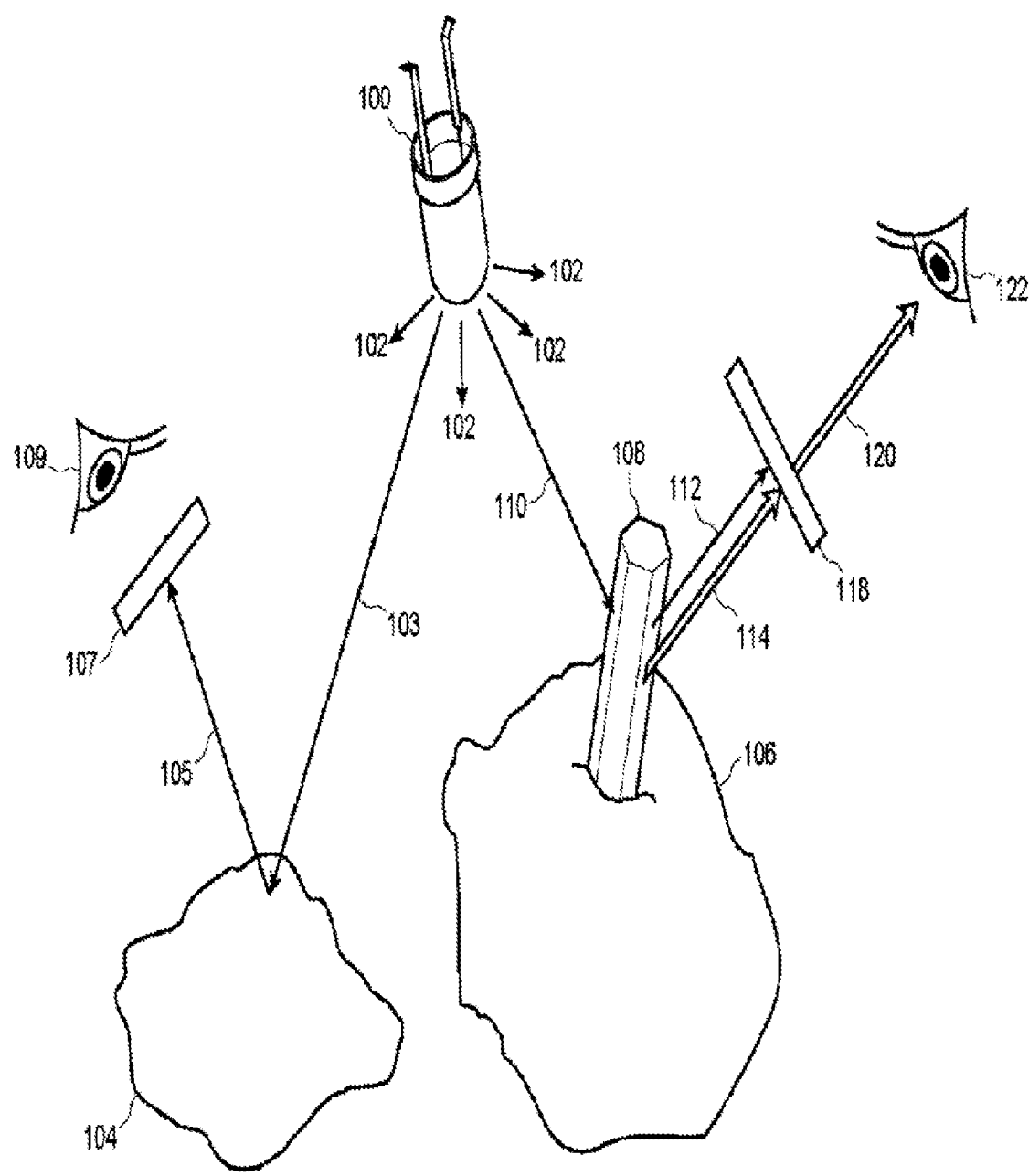
FIG. 7 is a view of the present invention as applied to a mining environment.

FIG. 7 depicts the method of the present invention being applied to separate valuable gem bearing ore from worthless background ore being produced in a mine for example. A narrow band red incident light source 100, such as a red light LED peaking at 635 nanometers is shown with rays 102 and having ray 103 impinging on ore samples 104 and ray 110 on ore sample 106. Sample 104 has no gem content, and as a result merely reflects the impinging light directly as shown at 105. A red light filter 107 which is configured to block red light across the range of light produced by the incident light source, passes no light to the observer 109. In other words, when observed through the filter 107 the ore sample 104 remains dark. However, when observed without the filter the whole ore sample 104 appears red due to the reflected light.

In contrast, the ore 106 contains some chromium bearing gem material. This is illustrated as 108. Upon the incident red light 110 impinging on the gem material 108, both red light 112 and red light fluorescence 114 result. The reflected red incident light 112 is blocked by the filter 118 but the red light fluorescence ray 120 passes and is observed at 122. In other words, when the illuminated ore is observed through the appropriate red light filter, the fluorescing gem is very visible and easily distinguished. On the other hand, when observed by the naked eye, all that can be seen is the whole ore sample as red, due to the incident red light being reflected off the ore sample. A broad spectrum or crude red light filter will not work as it must be precise enough to pass visible red light fluorescence at wavelengths above the incident light while blocking the red incident light.

Figure 8:
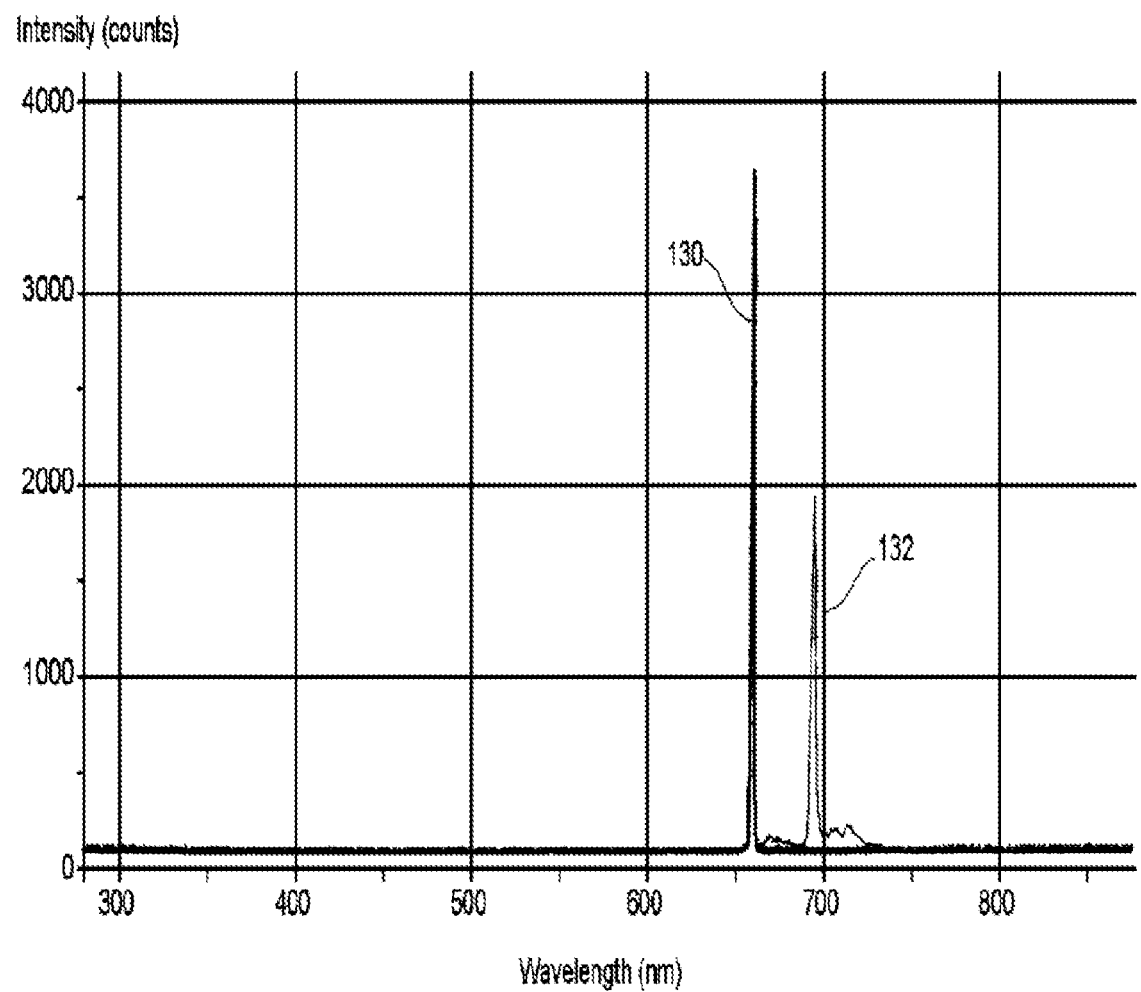
FIG. 8 is a plot of a red laser incident light source, applied to a flame fusion synthetic ruby.

FIG. 8 is a plot of a red light laser incident light source shown as 130 impinging on a synthetic flame fusion ruby which gives of a red light fluorescence as shown by trace 132 centered on wavelength just below 700 nms.

Figure 9:
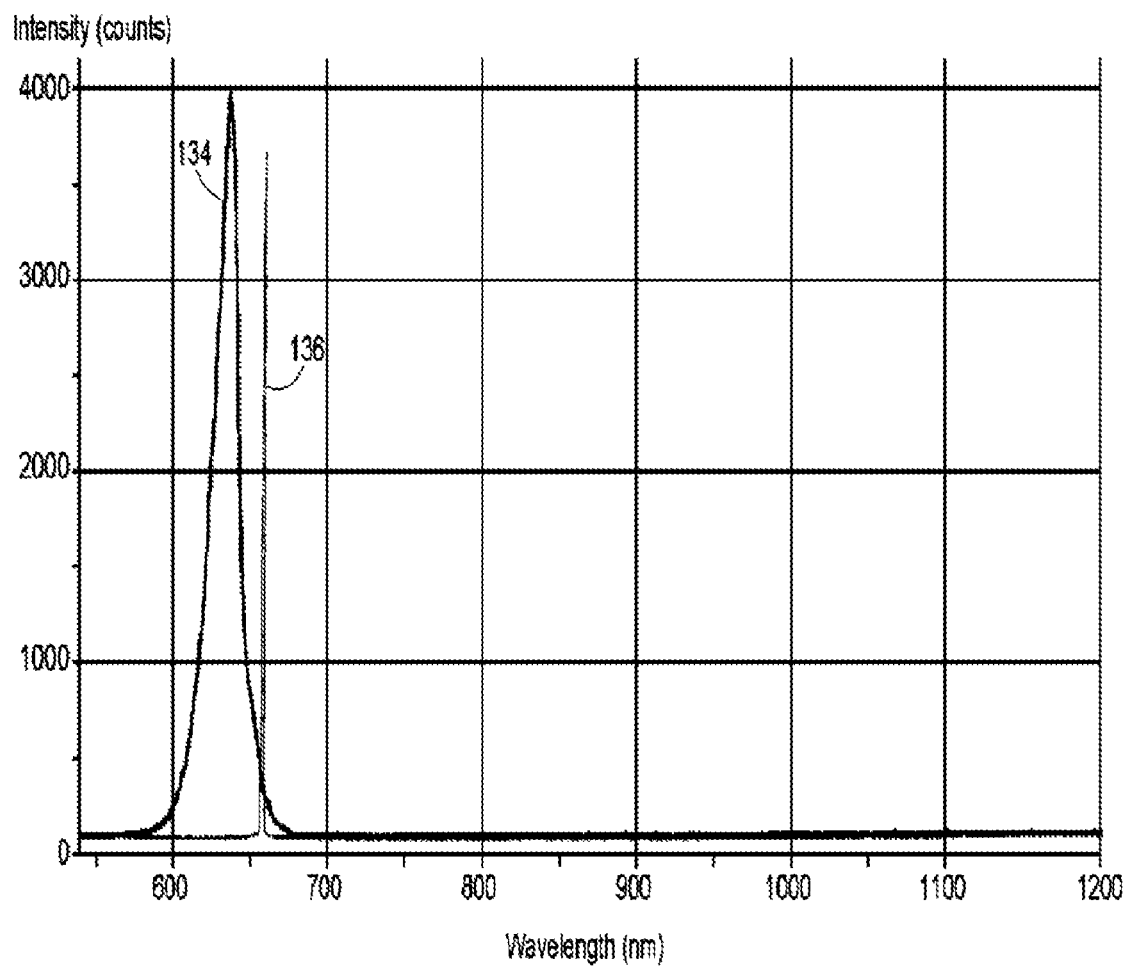
FIG. 9 is a plot of a red LED light source overlayed on a red laser light source.

FIG. 9 is a plot of two different suitable incident red light sources according to the present invention. The trace line 134 is for a LED light source and the line 136 is a laser light source. Red light LEDs are widely available from a number of manufacturers, as are pocket laser pointers. While each one will likely have different wavelength distributions, even with the same brand, a suitable one will be characterized as producing red light of sufficient intensity to elicit a fluorescing response from fluorescing materials, wherein the incident red light has a sufficiently short red light wavelength so as to permit the longer red light fluorescence to be within the visible spectrum.

The present invention can be used to characterize a number of materials providing they red fluoresce and this has been observed in certain natural materials such as emeralds, rubies, pink sapphires, alexandrites, spinnel, garnets, and tourmaline. The present invention can also be used to characterize a number of manmade materials, providing they red fluoresce, and this has been observed in materials such as certain coated manmade diamonds or other synthetic gem stones such as man made rubies and emeralds and other materials which exhibit the property of red light fluorescence. The other materials include certain forms of material or fabric as well. As will be appreciated by those skilled in the art, not every gem has the same composition. Thus, certain gems are known to be inactive or non-fluorescing, even if they are from a class of gems that would be typically considered active. This is due to the peculiarities of the mineralization that occurs in nature in forming the gems in the first place including iron quenching of fluorescence. Thus, the present invention is of course limited to being used on those gems or other materials which exhibit the red light fluorescence property.

It can now be appreciated that the red light fluorescence that can be elicited from a red light incident source has certain advantages. The red light fluorescence is masked in a red incident light environment. The advantage is that this makes it harder to detect with the naked eye. Also the red light luminescence produced by the object, such as a gem as noted in the examples, tends to be in a relatively narrow band located close to the wavelength of the incident light source and so requires a specific filter. However, these very properties are an advantage in a detection technique which is on the one hand reliable and yet on the other not visible to the naked eye, even with the help of crude filters. Thus, in a separation facility for ore from a mine, the whole facility can be lit with red light, which is bright enough to allow the workers to move around and accomplish the required physical tasks, but does not provide to the workers enough visual information to permit the workers to identify the valuable gem material.

Thus the present invention is directed to the realization that a red light incident source which includes red light wavelengths between 610 and 650 nms can be used on a object to detect fluorescence generally in a light band slightly above the incident light band, generally below 750 nms in wavelength and at least part of which is typically below 700 nms in wavelength. Such red light fluorescence is detectable with a specific wavelength filter which blocks light wavelengths generally below 650 nms, and this can be an effective method for sorting objects such as gem materials in, among other things, a mine or ore processing environment. In the event that more than one chromium bearing gem material is found in a particular site, all of them can be located with the red incident light. So, where emeralds and alexandrite are found together, both can be characterized by this method. Of course the present invention can also be used to characterize already cut and polished gems from other visually similar gem materials and from materials which do not fluoresce red by this method such as glass or the like.

While reference has been made to certain preferred embodiments of the present invention, this is by way of example only, and it will be appreciated by those skilled in the art that the true scope of the invention is broadly defined by the attached claims. For example, while certain red light LED and laser light sources have been identified, other red light sources are also comprehended. What is required is that the red light source have a sufficient intensity to provoke fluorescence, and be of a wavelength to permit a longer red fluorescent light wavelength to be produced, most preferably in the easily visible red light range.

The Canadian patent application filed Aug. 24, 2007 by Sylvia Gumpesberger entitled "A Method and Apparatus for Identifying and Characterizing Objects based on Fluorescence" is incorporated herein in its entirety by reference.

I claim:

1. A method of characterizing objects, said method comprising the steps of:
   a) Illuminating said object with an incident red light having wavelengths shorter than a maximum red light wavelength, said object being characterized as exhibiting red light fluorescence of a longer wavelength than the wavelength of the incident light, wherein said red light fluorescence arises from said object due to the presence of chromium; and
   b) Detecting the presence of said longer wavelength red light fluorescence emanating from said object.

2. A method of characterizing objects as claimed in claim 1 wherein said step of detecting said red light fluorescence includes placing a filter between said object and a detector, said filter being characterized as blocking said incident red light but passing said longer wavelength red light fluorescence.

3. A method of characterizing objects as claimed in claim 2 wherein said step of detecting is done by eye.

4. A method of characterizing objects as claimed in claim 1 wherein said step of detecting is done by a detection device.

5. A method of characterizing objects as claimed in claim 4 wherein said detection device provides an output signal upon detecting the presence of red light fluorescence at a wavelength longer than said incident light.

6. A method of characterizing objects as claimed in claim 5 wherein said output signal is used to trigger an actuator to separate an object exhibiting said red light fluorescence from other objects not exhibiting said red light fluorescence.

7. A method of characterizing objects as claimed in claim 1 wherein said object is a natural material.

8. A method of characterizing objects as claimed in claim 1 wherein said object is a man made material.

9. A method of characterizing objects as claimed in claim 7 wherein said object is one or more of red light fluorescing emerald, alexandrite, ruby, pink and purple sapphire, red or pink spinel, pink topaz, garnet and tourmaline.

10. A method of characterizing objects as claimed in claim 8 wherein said object is a red light fluorescing synthetic ruby, emerald, alexandrite, colour change corundum and red or pink spinel and synthetic and coated diamonds.

11. An apparatus for sorting a stream of material, said stream of material comprising chromium-bearing gem material, the apparatus comprising:
   a conveyor belt,
   a source of red incident light including wavelengths of at least between 600 and 650 nms;

a station to apply the red incident light to said stream of material;

a detector to detect red light fluorescence in a wavelength between 650 and 700 nms due to the presence of said chromium-bearing gem material in said stream of material;

said conveyor belt configured to move said stream of material past said detector; and an arm or source of compressed air, said arm or source of compressed air configured to physically separate said chromium-bearing gem material from said stream of material.

12. A method of sorting a chromium containing object from a stream of objects, the method comprising the steps of
   a) illuminating said stream of objects with an incident red light having wavelengths shorter than a maximum red light wavelength, said chromium containing object being characterized as exhibiting red light fluorescence of a longer wavelength than the wavelength of the incident light;
   b) detecting the presence of said longer wavelength red light fluorescence emanating from said chromium containing object;
   c) removing said chromium containing object from said stream of objects.

13. The method of claim 12 wherein said chromium containing object is a gem.

14. The method of claim 13 wherein said chromium object is a red light fluorescing object selected from group consisting of emerald, alexandrite, ruby, pink sapphire, red spinel, pink spinel, pink topaz, garnet and tourmaline.

15. The method of claim 12 wherein said stream of objects includes gem bearing ore and non-gem bearing ore, said gem bearing ore comprising chromium, the method further comprising the step of moving said gem bearing ore and said non-gem bearing ore past the detector.

16. The method of claim 15 wherein said step of detecting is done by a detection device, said detection device providing an output signal upon detecting the presence of red light fluorescence at a wavelength longer than said incident light, and said output signal is used to trigger an actuator to remove said gem bearing ore from said non-gem bearing ore.

17. The apparatus of claim 11 wherein said stream of material is disposed on said conveyor belt.

* * * * *